US008512941B2

(12) United States Patent
Natan (10) Patent No.: US 8,512,941 B2
(45) Date of Patent: *Aug. 20, 2013

(54) BIOLOGICAL MATERIAL AND METHODS AND SOLUTIONS FOR PRESERVATION THEREOF

(75) Inventor: Yehudit Natan, Holon (IL)

(73) Assignee: Core Dynamics Limited, Hamilton (BM)

( * ) Notice: Subject to any disclaimer, the term of this patent is extended or adjusted under 35 U.S.C. 154(b) by 24 days.

This patent is subject to a terminal disclaimer.

(21) Appl. No.: 13/074,843

(22) Filed: Mar. 29, 2011

(65) Prior Publication Data

US 2011/0177488 A1    Jul. 21, 2011

Related U.S. Application Data

(63) Continuation-in-part of application No. 10/588,126, filed as application No. PCT/IL2005/000125 on Feb. 2, 2005, now Pat. No. 7,935,478.

(60) Provisional application No. 60/540,557, filed on Feb. 2, 2004, provisional application No. 60/577,210, filed on Jun. 7, 2004.

(51) Int. Cl.
*A01N 1/02* (2006.01)
*C12N 5/078* (2010.01)

(52) U.S. Cl.
USPC .............................................. 435/2; 435/374

(58) Field of Classification Search
None
See application file for complete search history.

(56) References Cited

U.S. PATENT DOCUMENTS

| | | | |
|---|---|---|---|
| 3,074,247 A | 1/1963 | Polk | |
| 3,347,745 A | 10/1967 | Rinfret et al. | |
| 3,548,051 A | 12/1970 | Dingwall | |
| 4,018,911 A | 4/1977 | Lionetti et al. | |
| 4,117,881 A | 10/1978 | Williams et al. | |
| 4,480,682 A | 11/1984 | Kaneta et al. | |
| 4,620,908 A | 11/1986 | Van Duzer | |
| 4,857,319 A | 8/1989 | Crowe et al. | |
| 4,874,690 A | 10/1989 | Goodrich, Jr. et al. | |
| 5,059,518 A | 10/1991 | Kortright et al. | |
| 5,071,598 A | 12/1991 | Baldeschwieler et al. | |
| 5,131,850 A | 7/1992 | Brockbank | |
| 5,364,756 A | 11/1994 | Livesey et al. | |
| 5,418,130 A | 5/1995 | Platz et al. | |
| 5,587,490 A | 12/1996 | Goodrich, Jr. et al. | |
| 5,629,145 A | 5/1997 | Meryman | |
| 5,827,741 A | 10/1998 | Beattie et al. | |
| 5,843,780 A | 12/1998 | Thomson | |
| 5,863,715 A | 1/1999 | Rajotte et al. | |
| 5,869,092 A | 2/1999 | Hays et al. | |
| 5,873,254 A | 2/1999 | Arav | |
| 5,897,987 A | 4/1999 | Oliver et al. | |
| 5,955,257 A | 9/1999 | Burger et al. | |
| 5,981,163 A | 11/1999 | Horowitz et al. | |
| 6,007,978 A | 12/1999 | Goodrich, Jr. et al. | |
| 6,073,540 A | 6/2000 | Garrett | |
| 6,146,890 A | 11/2000 | Danon | |
| 6,171,549 B1 | 1/2001 | Kent | |
| 6,319,914 B1 | 11/2001 | Simpkins et al. | |
| 6,337,205 B1 | 1/2002 | Wisniewski | |
| 6,453,683 B1 | 9/2002 | Wisniewski et al. | |
| 6,482,585 B2 | 11/2002 | Dottori | |
| 6,488,033 B1 | 12/2002 | Cerundolo | |
| 6,723,497 B2 | 4/2004 | Wolkers et al. | |
| 6,740,484 B1 | 5/2004 | Khirabadi et al. | |
| 6,887,704 B2 | 5/2005 | Peled et al. | |
| 7,422,737 B1 | 9/2008 | Nussinovitch et al. | |
| 7,935,478 B2 * | 5/2011 | Natan et al. ..................... | 435/1.3 |
| 8,198,085 B2 * | 6/2012 | Kanias et al. ................. | 435/374 |
| 2002/0119946 A1 | 8/2002 | Gen | |
| 2002/0177116 A1 | 11/2002 | Wiggins et al. | |
| 2003/0047515 A1 | 3/2003 | Keller | |
| 2003/0059338 A1 | 3/2003 | Mann et al. | |
| 2003/0068416 A1 | 4/2003 | Burgess et al. | |
| 2003/0083270 A1 | 5/2003 | Burdick et al. | |
| 2004/0006999 A1 | 1/2004 | Brown et al. | |

(Continued)

FOREIGN PATENT DOCUMENTS

| | | |
|---|---|---|
| DE | 100 56 181 C1 | 3/2002 |
| EP | 0 664 080 A1 | 7/1995 |

(Continued)

OTHER PUBLICATIONS

Csönge, et al., "Banking of osteochondral allografts, Part II. Preservation of Chondrocyte Viability During Long-Term Storage", Cell and Tissue Banking, vol. 3, pp. 161-168, (2002). XP-002313332.

Gao, et al., "Development of a Directional Solidification Device for Cell Cryopreservation", Cell Preservation Technology, vol. 1, No. 4, pp. 231-238, (2003).

Goodrich, et al., "Preservation of metabolic activity in lyophilized human erythrocytes", Proc. Natl. Acad. Sci. USA, vol. 89, pp. 967-971, (1992).

Han, et al., "Protection of osteoblastic cells from freeze/thaw cycle-induced oxidative stress by green tea polyphenol", Biotechnology Letters, vol. 27, pp. 655-660, (2005).

Higgs, et al., "Cartilage Regeneration and Repair, Where Are We?" Proceedings of the International Cartilage Repair Society's Second Symposium, (1998).

(Continued)

*Primary Examiner* — Jeffrey E Russel (74) *Attorney, Agent, or Firm* — Vorys, Sater, Seymour and Pease LLP; Susanne M. Hopkins; Ari G. Zytcer (57) ABSTRACT

Provided is a preservation solution for preserving biological material at low temperature including one or more polyphenols and a method for preservation of biological material, the method includes adding the preservation solution to biological material, cooling the biological material and storing it under appropriate storing conditions. The present method may be used for hypothermic preservation or for cryopreservation, including freezing and lyophilization, and may be used with any biological material, including cells selected from RBC, WBC, MNC, UCB MNC and bacteria. In the case of RBC, also disclosed is a method for its freezing such that upon thawing, the material has less than 2% free hemoglobin.

9 Claims, 5 Drawing Sheets

(56) References Cited

U.S. PATENT DOCUMENTS

| | | | |
|---|---|---|---|
| 2004/0067157 A1 | 4/2004 | MacPhee et al. |
| 2004/0129003 A1 | 7/2004 | Voute et al. |
| 2004/0191754 A1 | 9/2004 | Meir et al. |
| 2004/0197310 A1 | 10/2004 | Sanberg et al. |
| 2005/0008623 A1 | 1/2005 | Bechetoille et al. |
| 2005/0020524 A1 | 1/2005 | Boyd |
| 2005/0042754 A1 | 2/2005 | Miyazaki et al. |
| 2005/0059152 A1 | 3/2005 | Tanavde et al. |
| 2005/0095228 A1 | 5/2005 | Fraser et al. |
| 2005/0118712 A1 | 6/2005 | Tsai et al. |
| 2005/0142118 A1 | 6/2005 | Wernet |
| 2006/0035383 A1 | 2/2006 | Ho et al. |
| 2006/0057555 A1 | 3/2006 | Damari et al. |
| 2007/0077237 A1 | 4/2007 | Damari et al. |
| 2007/0277535 A1 | 12/2007 | Uri et al. |
| 2008/0120984 A1 | 5/2008 | Shaham et al. |

FOREIGN PATENT DOCUMENTS

| | | |
|---|---|---|
| EP | 0668013 A2 | 8/1995 |
| EP | 1 057 405 A1 | 12/2000 |
| EP | 1057405 A1 | 12/2000 |
| EP | 1 131 998 A1 | 9/2001 |
| EP | 1 471 140 A1 | 10/2004 |
| EP | 1 535 514 A1 | 6/2005 |
| EP | 1 627 565 A1 | 2/2006 |
| GB | 1279356 | 6/1972 |
| JP | 2000-189155 A | 7/2000 |
| RU | 1806692 A1 | 4/1993 |
| WO | 91/06213 A1 | 5/1991 |
| WO | 91/16060 A1 | 10/1991 |
| WO | 9300806 A1 | 1/1993 |
| WO | 97/35472 A1 | 10/1997 |
| WO | 9739104 A1 | 10/1997 |
| WO | 98/10231 A1 | 3/1998 |
| WO | 98/46072 A1 | 10/1998 |
| WO | 9960849 A1 | 12/1999 |
| WO | 00/29551 A2 | 5/2000 |
| WO | 01/23532 A1 | 4/2001 |
| WO | 01/45503 A2 | 6/2001 |
| WO | 01/50852 A1 | 7/2001 |
| WO | 01/87062 A2 | 11/2001 |
| WO | 0201952 A1 | 1/2002 |
| WO | 02/32225 A2 | 4/2002 |
| WO | 02/076206 A2 | 10/2002 |
| WO | 03020874 A2 | 3/2003 |
| WO | 03/056919 A2 | 7/2003 |
| WO | 03/099040 A1 | 12/2003 |
| WO | 2004/009138 A2 | 1/2004 |
| WO | 2004/055456 A1 | 7/2004 |
| WO | 2004/098285 A2 | 11/2004 |
| WO | 2005/032251 A1 | 4/2005 |
| WO | 2005/056755 A2 | 6/2005 |
| WO | 2005/072523 A2 | 8/2005 |
| WO | 2005/072790 A1 | 8/2005 |
| WO | 2006/016372 A1 | 2/2006 |
| WO | 2008032314 A2 | 3/2008 |

OTHER PUBLICATIONS

Jomha, et al., "Cryopreservation of intact human articular cartilage", Journal of Orthopaedic Research, vol. 20, pp. 1253-1255, (2002).

Kusakabe, et al., "Maintenance of genetic integrity in frozen and freeze-dried mouse spermatozoa", Proc Natl Acad Sci U S A, vol. 98, No. 24, pp. 13501-13506, (2001).

Kushibe, et al., "Tracheal Allotransplantation Maintaining Cartilage Viability with Long-Term Cryopreserved Allografts", Ann Thorac Surg, vol. 71, pp. 1666-1669, (2001).

Laprade, et al., "Refrigerated Osteoarticular Allografts to Treat Articular Cartilage Defects of the Femoral Condyles. A Prospective Outcomes Study", J Bone Joint Surg Am, vol. 91, pp. 805-811, (2009).

López, et al., "Determination of Viability of Human Cartilage Allografts by a Rapid and Quantitative Method Not Requiring Cartilage Digestion", Cell Transplantation, vol. 17, pp. 859-864, (2008).

McGoveran, et al., "Long-Term Chondrocyte Viability in a Fresh Osteochondral Allograft", The Journal of Knee Surgery, vol. 15, No. 2, pp. 97-100, (2002).

Muldrew, et al., "Localization of Freezing Injury in Articular Cartilage", Cryobiology, vol. 31, pp. 31-38, (1994).

Muldrew, "Cryopreservation of Articular Cartilage", Abstracts, 33rd Annual Meeting of the Society for Cryobiology, pp. 616-617, No. 6, Indianapolis, Indiana, Aug. 21, 1996.

Muldrew, et al., "Cryobiology of Articular Cartilage: Ice Morphology and Recovery of Chondrocytes", Cryobiology, vol. 40, pp. 102-109, (2000).

Muldrew, et al., "Transplantation of Articular Cartilage Following a Step-Cooling Cryopreservation Protocol", Cryobiology, vol. 43, pp. 260-267, (2001).

Muldrew, et al., "Chondrocyte Sensitivity to Lethal Injury Correlates with Proximity to the Cartilage Surface", Abstracts, 32nd Annual Meeting of the Orthopaedic Research Society, pp. 589, No. 136, New Orleans, Louisiana, Feb. 1986.

Pegg, et al., "Fractures in Cryopreserved Elastic Arteries", Cryobiology, vol. 34, pp. 183-192, (1997).

Rzepakovsky, "The Effect of Long Term Storage at -80° C. on the Cell Viabillity in Cartilage Tissue", Study Report, No. LAB-0161, 3 pages, (2005).

Rzepakovsky, "The Effect of Long Term Storage in Liquid Nitrogen on the Cell Viabillity in Cartilage Tissue", Study Report, No. LAB-0161, 3 pages, (2006).

Schachar, et al., "Transplantation of Cryopreserved Osteochondral Dowel Allografts for Repair of Focal Articular Defects in an Ovine Model", The Journal of Bone and Joint Surgery, Inc., vol. 17, pp. 909-920, (1999).

Dimethyl sulfoxide, SIGMA Product Information, 2 pages, Dec. 2003.

Teng, et al., "Enhancing Osteochondral Allograft Viability", Clin Orthop Relat Res, vol. 466, pp. 1804-1809, (2008).

Towns, "Moisture content in proteins: its effects and measurement", Journal of Chromatography A, vol. 705, pp. 115-127, (1995).

Van Steensel, et al., "Optimization of cryopreservative procedures for human articular cartilage chondrocytes", Arch Orthop Trauma Surg, vol. 113, pp. 318-321, (1994).

Williams, et al., "Prolonged Storage Effects on the Articular Cartilage of Fresh Human Osteochondral Allografts", J Bone Joint Surg Am, vol. 85, pp. 2111-2120, (2003).

Williams, et al., "Analysis of Cartilage Tissue on a Cellular Level in Fresh Osteochondral Allograft Retrievals", Am J Sports Med, vol. 35, No. 12, pp. 2022-2032, (2007).

Williams, et al., "Controversies in Knee Surgery", Controversies in Orthopaedic Surgery, pp. 462-463, Oxford University Press, 2004.

Zoberi, et al., "Radiosensitizing and anti-proliferative effects of resveratrol in two human cervical tumor cell lines", Cancer Letters, vol. 175, pp. 165-173, (2002).

Lelkens, et al., "Stability after thawing of RBCs frozen with the high- and low-glycerol method," Transfusion, (2003), vol. 43, pp. 157-164, The Military Blood Bank, Netherlands.

Chow, et al., "Phase I pharmacokinetic study of tea polyphenols following single-dose administration of epigallocatechin gallate and polyphenon E1," Cancer Epidemiology, Biomarkers & Prevention, (2001), vol. 10, pp. 53-58, The University of Arizona.

De Korte, et al., "Quality determinants of erythrocyte destined for transfusion," Cellular and Molecular Biology, (2004), vol. 50, No. 2, pp. 187-195.

Grinberg, et al., "Protective effects of tea polyphenols against oxidative damage to red blood cells," Biochemical Pharmacology, (1997), vol. 54, pp. 973-978, Elsevier Science Inc.

Galati, et al., "Prooxidant activity and cellular effects of the phenoxyl radicals of dietary flavonoids and other polyphenolics," Toxicology, (2002), vol. 177, pp. 91-104, Elsevier Science Inc.

Chen, et al., "Beneficial Effect of intracellular trehalose of the membrane integrity of dried mammalian cells," Cryobiology, (2001), vol. 43, pp. 168-181, Elsevier Science (USA).

Fujiki, et al., "Mechanistic findings of green tea as cancer preventive for humans," P.S.E.B.M., (1999), vol. 220, pp. 225-228, Society for Experimental Biology and Medicine.

Crowe, et al., "Stabilization of membranes in human platelets freeze-dried with trehalose," Chemistry and Physics of Lipids, (2003), vol. 122, pp. 41-52, Elsevier Science Ireland Ltd.

Satpathy, et al., "Loading red blood cells with trehalose: a step towards biostabilization," Cryobiology, (2004), vol. 49, pp. 123-136, Elsevier, Inc.

Kumazawa, et al., "Direct evidence of interaction of a green tea polyphenol, epigallocatechin gallate, with lipid bilayers by solid-state nuclear magnetic resonance," Biosci. Biotechnol. Biochem., (2004), vol. 68, No. 8, pp. 1743-1747.

Ahlenstiel, et al., "Bioflavonoids attenuate renal proximal tubular cell injury during cold preservation in Euro-Collins and University of Wisconsin solutions," Kidney International, (2003), vol. 63, pp. 554-563, International Society of Nephrology.

Suganuma, et al., "Green Tea and cancer chemoprevention," Mutation Research, (1999), vol. 428, pp. 339-344, Elsevier Science B.V.

Isbrucker, et al., "Safety studies on epigallocatechin gallate (EGCG) preparations. Part 3: teratogenicity and reproductive toxicity studies in rats," (2006), vol. 44, pp. 651-661. (Abstract).

XP-002337043, Derwent, "Preservation solution for cells and tissues contains polyphenol as effective component," (2004).

XP-002337044, Derwent, "Composition for preservative of animal cell, organs such as skin, blood vessel, cornea, kidney, heart, liver, lungs, placenta or pancreas, contains preset amount of epigallocatechin gallate as active ingredient," (2003).

* cited by examiner

% Membrane Integrity

BIOLOGICAL MATERIAL AND METHODS AND SOLUTIONS FOR PRESERVATION THEREOF

This application is a Continuation-In-Part Application filed under 35 U.S.C. §120 of U.S. patent application Ser. No. 10/588,126, filed on Aug. 23, 2006, which was an application filed under 35 U.S.C. §371 as a national stage of PCT/IL2005/000125, filed on Feb. 2, 2005, which was an application claiming the benefit under 35 U.S.C. §119(e) of U.S. Provisional Application No. 60/540,557, filed on Feb. 2, 2004, and an application claiming the benefit under 35 U.S.C. §119(e) of U.S. Provisional Application No. 60/577,210, filed on Jun. 7, 2004.

FIELD OF THE INVENTION

This invention relates to the preservation of biological material, including hypothermic preservation, freezing and lyophilization. More specifically, it relates to the composition of the media in which the biological material is preserved. The invention also relates to a method of preservation of the biological material to improve its survival after storage and/or the cryopreservation process.

LIST OF REFERENCES

The following references are considered to be pertinent for the purpose of understanding the background of the present invention:
1. WO 03/020874, Improved Method for Freezing Viable Cells;
2. WO 99/60849, Cryopreservation of Human Red Blood Cells;
3. U.S. Pat. No. 5,827,741, Cryopreservation of Human Adult and Fetal Pancreatic Cells and Human Platelets;
4. U.S. Pat. No. 6,723,497, Therapeutic Platelets and Methods;
5. U.S. Pat. No. 5,869,092, Prevention of leakage and phase separation during thermotropic phase transition in liposomes and biological cells;
6. Chen et al. 2001, *Beneficial effect of intracellular trehalose on the membrane integrity of dried mammalian cells*. Cryobiology 43(2):168-81.
7. Crowe et al. 2003, *Stabilization of membranes in human platelets freeze-dried with trehalose*. Chem. Phys. Lipids. 122(1-2):41-52.
8. De Korte and Verhoeven 2004, *Quality Determinants of erythrocyte destined for transfusion*. Cell. Mol. Biol. 50(2): 187-195.
9. Fujiki et al. 1999, *Mechanistic Findings of Green Tea as Cancer Preventive for Humans*. Proc. Soc. Exp. Biol. Med. 220(4) 225-228;
10. Goodrich et al. 1992, *Preservation of metabolic activity in lyophilized human erythrocytes*. Proc Natl Acad Sci USA. 89(3):967-71.
11. Kumazawa et al. 2004, *Direct evidence of interaction of a green tea polyphenol, epigallocatechin gallate, with lipid bilayers by solid-state Nuclear Magnetic Resonance*. Biosci Biotechnol Biochem. 68, 1743-7.
12. Lelkens et al. 2003, *Stability after thawing of RBCs frozen with the high and low glycerol method*. Transfusion 43:157-364.
13. Satpathy et al. 2004, *Loading red blood cells with trehalose: a step towards biostabilization*. Cryobiology 49(2): 123-36.
14. Suganuma et al. 1999, *Green Tea and Chemprevention* Mutation Research 428, 339-344.
15. Sherry Chow et al. 2001, Cancer Epidemiology, Biomarkers & Prevention 10, 53-58

BACKGROUND OF THE INVENTION

Biological material is often kept at low temperatures to prevent damage that may be caused from biological processes during storage. For a relatively short period of storage (normally up several to weeks) the material may be kept at low temperatures that are above freezing (hypothermic preservation). For example, red blood cells (RBC or erythrocytes) are usually stored for up to 42 days in a refrigerator at about 4° C., after which they must be discarded because RBC recovery falls below acceptable levels.

Preservation at a temperature below 0° C. (defined herein as "cryopreservation"), allows much longer storage times and may be at any temperature below 0° C., including such temperatures below −20° C., −70° C., −135° C., or in liquid nitrogen. Cryopreservation is achievable by freezing or by vitrification. In vitrification, ice-crystals are not formed, however high concentrations of potentially toxic cryoprotectant agents must be added to the biological material. These cryoprotectant agents must be removed before the biological sample is used, in order not to harm the recipient of the biological material. Freezing is also known to cause damage. For example, ice crystals forming in the solution exert extracellular mechanical stress. Intracellular stress can be caused for example by osmosis of water into the extra-cellular space, to replace water that is already frozen.

One factor that has a major effect on the success of cryopreservation is the composition of the solution in which the biological material is immersed prior to freezing. Currently many different cryopreservation solutions are known. Normally, such solutions contain a balanced salt solution such as phosphate buffered saline (PBS) and cryoprotectant agents (CPAs). Most freezing solutions comprise cryoprotectants selected from dimethyl sulfoxide (DMSO) and one or more polyalcohols such as glycerol, ethylene glycol, propylene glycol, and other molecules including butanediol and methanol. In addition, sugars, proteins, carbohydrates such as hydroxy ethyl starch (HES), dextran and other macromolecules are also used. Trehalose, for example, is thought to be protective by binding to lipid polar groups and replacing water. In addition, in WO 99/60849 for example it was claimed that addition of biochemistry altering reagents would reduce hemolysis of RBC during the freeze-thaw cycle.

For example, the current freezing method for RBC employs the addition of glycerol at high concentrations. There are two main methods for freezing with glycerol: high glycerol method (HGM) where the final concentration of glycerol is almost 40% and low glycerol method (LGM) where the final glycerol concentration is 19%. When HGM is used storage is done at −80° C. freezers, whereas, when using LGM storage is done in LN (−196° C.). Since, glycerol is toxic it has to be washed out after thawing. This is done in a process known as "de-glycerolization", wherein the thawed RBC are centrifuged, the supernatant removed and the pellet suspended in a glycerol free solution. This is normally repeated 3 times with decreasing sodium chloride concentrations (staring with 12% NaCl, then 1.6% NaCl and 0.9% NaCl) in order that intra-cellular glycerol be removed. Furthermore, as this process typically takes about 60 minutes, it renders frozen blood supplies an impractical solution for emergency use.

One problem associated with preservation of RBC is free hemoglobin in the sample, which increases with storage time and with damage to RBC. Free hemoglobin is hemoglobin that is not within an RBC and is considered undesirable in RBC samples for transfusion, not only because it is indicative of hemolysis (i.e. damage to RBC) but also since it in itself is hazardous to the recipient. It is normally calculated as the percent of supernatant hemoglobin from the total amount of hemoglobin in the sample. Current regulatory requirements in the United States from RBC for transfusion include that there be less then 1% free hemoglobin in the serum and that 75% of the cells need to be circulating 24 h after transfusion in vivo (De Korte et al. 2004). European regulations place a higher demand—that free hemoglobin be less than 0.8%.

The post-thaw hemolysis measured after thawing (but before washing) of RBC frozen in HGM or LGM are 4.4±1.0% and 10±2.0%, respectively (Lawns et al. 2003). Only after de-glycerolization (i.e. washing of the thawed cells) do the thawed RBC answer the quality demands for blood to be transfused. In WO 99/60849, frozen blood has less free hemoglobin, however this result is probably attributable to the use of (a) glycerol, (b) DMSO or (c) simultaneous use of many different CPAs.

In most cryopreservation protocols, preservation of the frozen biological material is at a temperature below $-130°$ C. This is normally done in containers of liquid nitrogen (LN) by either immersion of the biological material in LN or in LN vapor. This adds significantly to the cost of long-term preservation. In addition, incidents are known where the LN in the container evaporated (either due to a malfunction of the container or human error) and the biological materials were damaged.

One method that can overcome these obstacles is lyophilization of the frozen biological material (e.g. WO 03/020874). Lyophilization is a process in which ice crystals are removed by sublimation and desorption, resulting in dry matter. The lyophilized material may be stored at room temperature for a long period of time and be rehydrated for use by simply adding water. Lyophilization results in higher survival rates than air drying or heating, but is still a damaging process.

In order to enhance the biological material's ability to survive the freeze-drying process, intercellular and/or extracellular lyoprotectant agents (LPAs) are often added to the biological material. One such LPA is trehalose. It was shown, for example, that loading of platelets with trehalose, or with trehalose and DMSO, may improve their ability to withstand cryopreservation without premature inactivation (e.g. U.S. Pat. No. 5,827,741 and U.S. Pat. No. 6,723,497).

Commercial lyophilization of RBC is not performed and there is no known method or product that has been approved for use today. Goodrich R. P et al. (1992) carried out lyophilization of RBC and evaluated their enzymatic activity. They found that after lyophilization, most RBC enzymes have essentially maintained their concentrations. However, the two major organic phosphates ATP and 2,3-diphosphoglyceric acid (2,3-DPG), had reduced intra-cellular concentrations. In U.S. Pat. No. 4,874,690 free hemoglobin was not reported. However, the hemoglobin recovery level and the cell recovery levels were no more than 70%. This indicates that at least 30% of the cells fractured in these experiments and that the free hemoglobin was at least 30%.

Another approach to lyophilization of cells is the introduction of trehalose into cells. Trehalose is known to protect cell membranes in a dry state (Chen et al., 2001). It was also shown to improve platelet survival after freeze-drying (Crowe et al., 2003). Satpathy G R. et al. (2004), have introduced trehalose into RBC, although they did not attempt to freeze them, and evaluated the effect and loading method on RBC. They found that uptake of trehalose increases with its concentration, but that concomitantly hemolysis also increases significantly.

U.S. Pat. No. 6,770,478 discloses a method for the introduction of trehalose into cells by depletion of cholesterol from the RBC membrane, thus allowing for the trehalose to enter the cells. In this patent only membrane properties of RBC were evaluated and not the recovery of the cells (in terms of cells number and plasma free hemoglobin) after freeze-drying. However, Satpathy G. R. et al. (2004), have showed that introduction of trehalose into RBC causes significant hemolysis. In fact, this work showed that hemolysis was a result if introducing trehalose into the cells since hemolysis occurred in fresh RBC, since they did not freeze or freeze-dry the cells.

Apart from RBC, other cell types are known to populate blood. These are normally referred to as white blood cells (WBC), including monocytes, lymphocytes, granulocytes, platelets and macrophages. Lymphocytes (B lymphocytes and T lymphocytes), under normal conditions, make up about 20 to 35% of all white cells, but proliferate rapidly in the face of infection. Monocytes ordinarily number 4% to 8% of the white cells.

Umbilical cord blood (UCB) is a source for hematopoietic stem cells (HSC). HSC are cells that can differentiate into all blood cells. Other sources for HSC are bone marrow and very small amount of HSC can be found circulating in peripheral blood (as WBC). Morphologically, HSC have a round nucleus similar to the mononuclear white blood cells (lymphocytes and monocytes). They resemble lymphocytes very much, and may be slightly bigger. The method to differentiate between them is according to cell membrane antigens. HSC are normally identified by expression of the CD34 antigen. HSC (from peripheral blood, bone marrow or UCB) are given to patients whose immune systems has been damaged, e.g. due to chemotherapy and/or radiotherapyin and in different diseases such as: acute and chronic leukemias, myelodysplastic syndromes, Hodgkin lymphoma, non-Hodgkin lymphoma, and multiple myeloma, aplastic anemia, thalassemia, sickle cell anemia, neuroblastoma and more.

The current method for the preservation of HSC is using 10% DMSO and storage in liquid nitrogen (LN). When storing HSC from UCB and from peripheral blood the cells are separated using ficol-paque and the fraction that is stored are the MNC.

Epigallocatechin gallate (EGCG) is a polyphenol (MW 458.4) found naturally for example in green and black tea. The well-known beneficial effects associated with such tea are attributed, at least in part, to EGCG. Among the mechanisms associated with EGCG's beneficial effects are its ability to function as an antioxidant, its ability to associate with the phospholipids bi-layer of the cell membrane (Fujiki et al. 1999) and the lipid head groups of liposomes (Kumazawa et al., 2004) and more. Whilst EGCG is the main constituent of green tea, other polyphenols that are found naturally in green tea, such as epicatechin gallate (ECG) epigallocatechin (EGC) and epicatechin (EC), are also found in green tea and, like EGCG, are considered to be non-toxic. These polyphenols share structural and functional properties with EGCG (Suganuma et al. 1999).

SUMMARY OF THE INVENTION

Some terms used herein and their meanings are as follows:

The term "preservation" denotes the process of maintaining biological material under conditions in which its biological activity is considerably reduced while it nonetheless remains viable and may resume essentially normal biological activity when taken out of the preservation state. Specific examples of preservation are hypothermic preservation and cryopreservation.

The term "preservation solution" relates to a solution permitting the preservation of biological material, such that it retains its viability. A specific embodiment of a preservation solution is one for preserving biological material at low temperature. Such solution comprises such components that would allow the biological material to endure the preservation and, at times, also sustain the biological material, while being preserved. It would normally comprise a balanced salt solution such as phosphate buffered saline (PBS) or Sodium Chloride (NaCl) and other constituents that are known to improve the biological material's ability to withstand preservation conditions. Hypothermic preservation solutions and cryopreservation solutions are examples of preservation solutions.

The term "hypothermic preservation" means preservation at a temperature below the physiological temperature but above freezing, wherein biological processes are slowed down thus allowing prolonged storage of biological material (normally below 8° C. and above 0° C., and often between 4° C. and 8° C.).

The term "hypothermic preservation solution" means a preservation solution comprising such components that would allow the biological material to withstand a temperature below 8° C. and the necessary metabolites to sustain its viability at such temperature. It may include a balanced salt solution such as phosphate buffered saline (PBS) or a salt (e.g. 0.9% NaCl and one or more energy sources (such as sugar, adenine, a phosphate source etc.). Additional components often used in hypothermic preservation solutions are one or more antibiotics and, in the case of blood samples, also an anti-coagulant. Known examples for such hypothermic preservation solutions are CPDA-1 (sodium citrate, citric acid, monobasic sodium phosphate and adenine), and. ADSOL (Baxter, USA) which are used for hypothermic storage of RBC.

The term "cryopreservation" denotes a process including at least one step of lowering the temperature of biological material from a temperature that is above the freezing temperature of the biological material (or the solution in which it is immersed) to a temperature that is below that freezing temperature. Cryopreservation encompasses freezing, vitrification and lyophilization. The term "cryopreservation solution" refers to any solution or media in which a biological material is immersed before cryopreservation. Typically, cryopreservation solutions contain a balanced salt solution such as phosphate buffered saline (PBS) or NaCl and at least one (intracellular and/or extra-cellular) cryoprotectant agent (CPA) or intracellular and/or extra-cellular lyoprotectant agent (LPA) or polyalcohol. A cryopreservation solution may be a freezing solution, a vitrification solution, a lyophilization solution and/or a mixture of such solutions.

The term "freezing" denotes a process of cryopreservation that causes the formation of ice crystals within the frozen material.

The term "appropriate freezing conditions" means such freezing conditions that would maintain cells of a biological material in a viable state. In the relevant cases, in case of RBC, such a solution would not cause free hemoglobin, after thawing, to be above any given percentage, for example, resulting in post-preservation free hemoglobin levels below 10 percent. Such conditions relate to the freezing solution and its constituents (e.g. a conventional freezing solution with added polyphenols that optionally does not comprise a significant amount of a polyalcohol CPA and/or glycerol and/or DMSO and/or other undesired chemicals such as ethylene glycol, propylene glycol and other alcohols, butandiol and methanol), the freezing protocol including rate of cooling, temperature regime, directional freezing or stationary freezing, and the like. Non-limiting embodiments for such appropriate conditions include those embodiments and examples described herein.

The term "freezing solution" refers to any solution or media in which biological material is immersed before freezing. It comprises constituents that are intended to maintain the biological material whilst reducing the damage caused to the biological material by freezing and/or thawing. Freezing solutions normally comprise intercellular and/or extra-cellular CPAs.

The term "lyophilization" or "freeze-drying" denotes a process of cryopreservation in which the biological material is being frozen and dried. Thus, in the present invention wherever biological material is said to be freeze-dried or lyophilized, this may mean that at least two steps were executed, one of which for freezing the material and the other for drying.

The term "lyophilization solution" refers to any solution or media in which a biological material is immersed before lyophilization. Typically, lyophilization solutions contain constituents that are intended to maintain the biological material whilst reducing the damage caused to the biological material by freezing, drying, during storage and/or re-hydrating. Lyophilization solutions normally comprise one or more intercellular and/or extra-cellular LPAs. Lyophilization normally begins as primary drying (wherein water content of the biological material is reduced by 90-95%) and then secondary drying (wherein water content is reduced below 90-95%).

The term "cryoprotectant agent" denotes any agent that is added to a solution it improves the post thaw viability of a biological material cryopreserved in that solution. Intracellular CPAs are thought to replace water inside the cells, thus preventing crystallization therein, to enlarge the un-frozen fraction of the frozen solution, to buffer osmolarity and/or to stabilize the membrane and prevent mechanical damage caused by ice crystals. Examples of CPAs are DMSO, glycerol, ethylene glycol, poly ethylene glycol, propylene glycol, sugars, such as sucrose, dextrose, trehalose, and proteins, carbohydrates such as hydroxy ethyl starch (HES), dextran, etc.

The term "lyoprotectant agent" means a substance that is added to a solution and stabilizes biological material during lyophilization in said solution and/or during storage and may result in higher viability rates. Examples of LPAs include antioxidants, sugars, membrane stabilizers, high molecular weight molecules, etc.

The term "biological material" denotes cells, cell aggregates, tissue, organs, biological fluids and any other membranous entity such as liposomes (natural or synthetic). Such biological material may comprise, without limitation, any of the following: whole blood or fractions thereof, red blood cells (RBC), white blood cells (WBC), umbilical cord blood (UCB) or fractions thereof, UCB cells, stem cells, bone marrow, oocytes, sperm, ova, embryos, cartilage, ovary, heart, skin, kidney, liver, lung. In addition, such biological material may comprise cellular organisms, which may be eukaryotes or prokaryotes, including bacteria, and yeast, etc. Additionally, biological material may also comprise whole multi-cellular organisms that are capable of surviving cryopreservation such as nematodes. Fractions of blood may comprise any fraction of blood comprising blood cells (white and/or red), plasma and/or solutes and/or sub-cellular components (e.g. fractions of cells, such as platelets, components of degraded cells, etc.), proteins, lipids, antibodies, etc.

The term "viable biological material" means biological material comprising some viable cells or fractions of cells that are metabolically active or would become metabolically active after their release from the preservation state. Preferably in viable biological material at least 10% of the cells are viable cells, or preferably at least 30% or 50% and more preferably above 75%. In the case of RBC for example a preferred percentage of viable cells may be in some cases more than 75%. Preservation may be ceased using many different processes that should be chosen to suit the method of preservation and the nature of the biological material, including raising the temperature of the biological material, hydration of lyophilized biological material and/or removal of solutes. In case of biological material that does not comprise cells the term "viable" means that the material has maintained its structural integrity such that it maintains its biological function, or would do so after being removed from preservation.

The term "wash" (or "washing") in the context of the present invention means a process wherein cells are removed from a solution in which they are immersed and suspended in a new solution at least once, twice or more.

The term "polyphenol(s)" denotes both natural and/or synthetic polyphenol. Examples include catechins, such as those naturally found in green tea. Examples of catechins are epigallocatechin gallate (EGCG), epicatechin gallate (ECG) epigallocatechin (EGC) epicatechin (EC), DL-Catechin (DL-C) gallocatechin gallate (GCG), and including any other catechin, natural or synthetic and any mixture thereof. The term "polyphenols" also denotes, without limitation, green tea extract (GTE) that comprises catechins as well as any catechin-comprising fraction thereof. Smaller amounts of catechins are also found in other sources such as black tea, grapes and wine. When biological material is claimed in the context of this invention as comprising polyphenols, the amount of polyphenols is in excess of the amount naturally found in the relevant biological material.

The present invention is based, among other things, on the inventors' discovery that EGCG protects biological material during cooling, cycles of freezing and thawing, freeze-drying and hydrating. One of the benefits of using EGCG is that this compound, and to a lesser extent the other polyphenols, are considered beneficial food additives and as such may not need to be removed from the biological material before the biological material is used.

According to one aspect of the invention, a method for preservation of biological material is disclosed, said method comprising:
(a) adding a preservation solution to said biological material, said preservation solution comprising one or more polyphenols;
(b) cooling the biological material; and
(c) storing the biological material at appropriate storing conditions.

In some embodiments of the invention, small amounts of one or more polyalcohols, e.g. glycerol, that are conventionally used in preservation of biological material, particularly in preservation procedures involving cooling to below freezing, may be included in the preservation solution. However, it was surprisingly found in accordance with the invention that it is possible to preserve biological material even without use of polyalcohols in the preservation solution. The preservation solution used in accordance with the invention is thus preferably essentially free of any such polyalcohols, e.g. glycerol. The term "essentially free" should be understood as meaning free of any polyalcohols such as glycerol, or that any amount of polyalcohol present in the solution is so low so as not to have any effect on the preservation process, on the outcome of the preservation process or on the properties of the biological material (for example the viability of living matter, e.g. cells, if such are included in such material) after it is taken out of the preservation conditions.

Thus, the present invention provides, by another aspect, a method for preservation of biological material, comprising:
(a) adding a preservation solution essentially free of any polyalcohol, to said biological material;
(b) cooling the biological material; and
(c) storing the biological material at appropriate storing conditions.

It was found that the biological material preserved in accordance with the invention can be preserved even if having a volume exceeding 1 ml without any substantial change in its properties, e.g. while maintaining the viability of living matter where such material includes living matter, for periods exceeding about 40 days and even exceeding 60 days. Thus, the present invention provides, by another aspect, a preserved viable biological material, having a volume exceeding 1 ml, preserved for a period exceeding 40 days.

The method of the present invention may be used for hypothermic preservation or for cryopreservation, including freezing and lyophilization, and may be used with any biological material, including cells selected from red blood cells (RBC), white blood cells (WBC), mononuclear cells (MNC), umbilical cord blood cells (UCB), hematopoietic stem cells (HSC) and bacteria.

The appropriate storing conditions of the present invention comprise any such conditions that maintain the biological material viable. Such conditions normally include the temperature, which in the case of frozen samples must be below 0° C., preferably below −20°, below −70° C., below −135° C., or below −190 (e.g. in LN). In case of hypothermic preservation, the temperature is normally between 8° C. and 0° C. In the case of lyophilized samples, the temperature may be any temperature above 0° C. (e.g. room temperature) or below 0° C., as long as, the material is kept away from humidity. Generally, dryer lyophilized biological material may be maintained at higher temperatures with minimal damage than material that is less dry. In addition, the nature of the components of the lyophilization solution affect the storage temperature, since storage is best if it is at such temperature when the components of the solution do not liquefy. Obviously the material should also be maintained in a sterile environment (e.g. a sealed test tube or bag) so that they do not become contaminated. It is appreciated that when the biological material is lyophilized and intended to be stored at a given temperature (e.g. room temperature), it is preferred that the preservation solution will not contain agents (e.g. CPAs or LPAs) that are liquid at the given temperature. Finally, it is recommended that storage be away from light and any other form of radiation (at all temperatures). A person skilled in the art of the invention would appreciate that the adding of the preservation solution may be done in one or more steps such that one or more of the solutions' components would be added separately. Preferably, but not necessarily, the preservation solutions would not contain substances that would need to be removed from the biological material prior to use.

According to a different aspect, the present invention provides a preservation solution for preserving biological material comprising one or more polyphenols.

The polyphenols used in the preservation solution of the present invention may include one or more catechins, such as EGCG, or be provided as green tea extract (GTE). EGCG may be added for example at any concentration between 0-1M, preferably between about 50 µM and about 4 mM. One of the benefits of the present invention is in that additives that are known to be hazardous or toxic, such as glycerol, other polyalcohols, DMSO or any other undesired chemicals conventionally used in preservation of biological material), need not be added.

A person skilled in the art of the invention would be able to adjust the contents of the preservation solution to the duration and purpose of preservation and the type of biological material to be preserved. For example, when the purpose is hypothermic preservation, the preservation solution is a hypothermic preservation solution. When the preservation is cryopreservation, the preservation solution is a cryopreservation solution. In such case the solution may be for example a freezing solution (in which case the biological material is frozen) or a lyophilization solution (in which case the biological material is lyophilized). Likewise, any physiologically acceptable buffer or salt may be used in addition to or instead of PBS or NaCl. Non-limiting examples of such buffers are Hepes Talp, RPMI-1640 and F-12. Examples of additional ingredients that may be used in the solution are macromolecules that may protect the cells from mechanical damage, such as sugar, including dextran (for example, 20%-30%). Another potential additive is trehalose (e.g. 0.1M).

Preferably, the preservation solutions would not contain substances that would need to be removed from the biological material prior to its use. It is also preferable that the preservation solution would contain only elements that are considered safe or are known to be found in blood without known hazardous effects. For example, EGCG was found circulating in blood of human subjects after consumption of green tea (Sherry Chow et al. 2001).

According to yet another aspect of the present invention, a method is disclosed for the preservation of biological material comprising RBC, termed hereunder "the low free Hemoglobin method". This comprises:

(a) freezing the biological material in appropriate freezing conditions; and
(b) storing the biological material at appropriate storing conditions.

The low free hemoglobin method is characterized in that after thawing in appropriate thawing conditions the free hemoglobin levels of the biological material are below 2 percent.

The appropriate freezing conditions of the low free hemoglobin method include for example use of a freezing solution, such as any of the freezing solutions of the present invention. The appropriate thawing conditions of the low free hemoglobin method are such that are shown not to cause the appearance of free hemoglobin in the material that exceed 2%. One example for such thawing would be incubation of the biological material in a water bath at about 37° C. until it appears visually to be thawed. Preferably it would be then moved directly to a lower temperature such as 4° C. or on ice. Non-limiting examples of such appropriate freezing and thawing conditions are provided in the embodiments exemplified hereunder.

According to one option, this low free hemoglobin method may also comprise a step of thawing the biological material and separating the thawed cells from the liquid in which they are suspended. This separation may be done for example by a single step of centrifugation or by filtration. The result of such separation is the obtaining of packed RBC (i.e. RBC with a hematocrit of 80% or more) which is a form of RBC that is readily transfused. Another term for this process may thus be packing of the RBC. Upon such separation, the levels of free hemoglobin are reducible to levels below 1.

Among the benefits of the low free hemoglobin method is the potential abandonment of the need to wash the thawed cells.

According to yet another aspect, the present invention also provides biological material comprising viable biological material and one or more polyphenols. Such polyphenols may include one or more catechins, such as EGCG, or be derived from green tea extract (GTE). One of the benefits of the present invention is the biological material may be essentially free of additives that are known to be hazardous or toxic, such DMSO or polyalcohols such as glycerol and other undesired chemicals such as ethylene glycol, propylene glycol and other alcohols, butandiol and methanol). The term "essentially free" means that the additive are less than 5%, preferably less than 3%. The biological material of the present invention may comprise cells selected from RBC, WBC, MNC, UCB, HSC is and bacteria, and may have any temperature, above or below zero including temperatures of cryopreservation or room temperature, providing that the biological material is viable. In addition, the biological material may be in a dry state or almost fully dry (comprising 10% or less of its original water content).

According to yet another option, frozen viable biological material is provided, comprising RBC and characterized in that after thawing in appropriate thawing conditions the free hemoglobin levels of the biological material are below 2 percent. This frozen viable biological material may or may not be frozen a preservation solution of the present invention.

The biological material of this invention may accordingly be provided in a hypothermic, frozen or freeze-dried state. It may also be provided in a revived viable form, after having been warmed, thawed and/or hydrated using any method known in the art that is compatible with the type and condition of the biological material.

Freeze-drying and cryopreservation in accordance with the present invention may be carried out in any method suitable to the biological material in question. The freezing of above methods of the present invention can be done in any method or apparatus known in the art. A preferred example would be using a directional freezing device such as that which is described in WO 03/020874. Nevertheless, any freezing method which allows cryopreservation of biological material may be used, including using mechanical freezers, stepwise freezing apparatus, the Planner freezing apparatus, slush freezing, freezing in cryogenic fluid, freezing in controlled rate freezers, liquid bath freezer or cold air freezers, etc. Likewise, the biological material may be treated additionally in one or more methods known in the art, such as those described in U.S. Pat. No. 5,827,741 or U.S. Pat. No. 6,723,497.

DETAILED DESCRIPTION OF THE INVENTION

In the following some non-limiting examples are provided, showing how the present invention may be practiced.

BRIEF DESCRIPTION OF THE DRAWINGS

In order to understand the invention and to see how it may be carried out in practice, preferred embodiments will now be described, by way of non-limiting example only, with reference to the accompanying drawings, in which:

FIG. 1. this is FIG. 2 depicts photographs, taken using a light microscope, showing of differential staining of RBC (erythrocytes) with May-Gruenwald Giemsa. A1 to A4 show RBC mixed 1:1 with a freezing solution containing 30% (w/v) Dextran and 0.412 mM EGCG. A1 shows fresh erythrocytes (×1000), A2 (×1000) and A3 (×400) are of frozen thawed erythrocytes and picture A4 (×1000) is of freeze-dried erythrocytes, after rehydration. B1 to B3 (×1000) depict erythrocytes frozen only with saline. B1 shows fresh erythrocytes, B2 and B3 show frozen thawed erythrocytes.

EXPERIMENTS

Materials and Methods

Unless otherwise noted, all materials were purchased from Sigma Inc. (St. Louis. Mo., USA) and PBS means phosphate buffered saline ($Ca^{+2}$ & $Mg^{+2}$ free).

1. Red Blood Cells (RBC)

The following procedures were used in all examples as relevant, unless specific modifications or other methods are detailed.

Preparation of Packed Red Cells

Red blood cells (RBC) were separated from whole blood received from the Israeli Blood Bank. The blood was centrifuged for 10 minutes at 1500 g and the plasma was discarded. The pellet was suspended in an equal volume of phosphate buffered saline (PBS) (Calcium and Magnesium free), and centrifuged again at 1500 g for 10 minutes. Afterwards the supernatant was discarded, and an equal volume of cryopreservation solution selected from the solutions in Table I was added to the packed RBC. Different volumes (2.5-50 ml) of the RBC suspension were transferred to a 16-25 mm diameter glass test tube (Manara, Israel). The experiment of freezing 200 ml of RBC suspension was done in a 2000 ml freezing bag (Baxter-Fenwal, USA). Samples were then either frozen and thawed in a water bath at 37° C. or lyophilized and rehydrated with double distilled water (DDW) at 37° C.

TABLE I

Components of Cryopreservation Solutions

| Solution name | PBS | Autologous Plasma | Dextran 40,000 Da. | HSA* | Trehalose | EGCG (mM) |
|---|---|---|---|---|---|---|
| Plasma | — | 100% | — | — | — | — |
| Saline | 100% | — | — | — | — | — |
| Dextran | 100% | — | 30%(w/v) | — | — | — |
| HSA + Trehalose | 50% | — | — | 50% | 0.1M | — |
| Trehalose | 100% | — | — | — | 0.1M | — |
| EGCG | 100% | — | — | — | — | 0.412 |
| EGCG + Dextran | 100% | — | 30%(w/v) | — | — | 0.412 |
| EGCG + HSA + Trehalose | 50% | — | — | 50% | 0.1M | 0.412 |
| EGCG + Trehalose | 100% | — | — | — | 0.1M | 0.412 |

*Human Serum Albumin

Freezing

Glass test tubes containing RBC were frozen in a modified MTG freezing apparatus, as described in WO 03/020874 (manufactured by IMT, Israel). The thermal gradient in the cooling unit was set to 5.5° C./mm or 10.5° C./mm or 15.5° C./mm (as detailed below) with final temperatures of −50° C., −100° C. or −150° C. The rate of test tube insertion (interface velocity) was 0.5, 1, 1.5 and 3 mm/sec, yielding calculated cooling rates of 165, 330, 500, 1000 or 2000° C./min. During freezing the test tubes that contained only 2.5 ml samples were rotated at a rate of 56 rpm. Subsequent to freezing, biological material was taken from each test tube to test for cell viability.

Lyophilization and Rehydration

Lyophilization was performed in a commercial lyophilizer (Labconco, USA) with a condenser temperature of −82° C. for 72 hours. The biological material was is rehydrated by adding DDW to reach the sample's original volume.

Thawing

Frozen (but not lyophilized) material was thawed by immersion in a water bath at 37° C. for until it melted. Melting was observed visually.

Assessment of Cell Survival a. Cell Count

Cells were counted using the PENTRA 60 cell counter (ABX, France), in accordance with the manufacturer's manual. This device provides a complete cell count (CBC) that includes parameters such as: cell number, hematocrit, mean cell volume, hemoglobin, etc.

b. Morphology Evaluations

Morphology evaluations of the erythrocytes were done by observation of a 5 µl drop of red blood cells under a light microscope (Zeiss, Germany) and by differential staining of May-Gruenwald Giemsa stains. In brief, cell suspensions were spread on a glass slide, and the slides were left to air dry. Then slides were fixed in absolute methanol for 2-3 minutes at room temperature. Afterwards, slides were stained for 15 minutes in May-Gruenwald stain (freshly diluted with an equal volume of distilled water, pH6.8). After 15 minutes the slides were stained for 10 minutes in Giemsa stain (freshly diluted with distilled water (1:9 ratio), pH6.8). Then the slides were washed in running tap water and left for 3-4 minutes in distilled water. The slides were then allowed to dry and were observed under a light microscope (Zeiss, Germany) using immersion oil.

Example 1

Freezing and Lyophilizing RBC at a Volume of 2.5 ml

Table II shows survival of RBC after freezing cells at 1,000 and 2,000° C./min. Column 1A depicts the results for cells that were frozen at 1,000° C./min and thawed but not lyophilized. Columns 1B depicts the results for cells that were frozen at 1,000° C./min and lyophilized, and were then rehydrated using DDW. Columns 2A and 2B respectively depict the results for cells that were frozen at 2,000° C./min and then either (A) thawed but not lyophilized or (B) lyophilized, and then rehydrated using DDW. The results are presented as the percentage of cells that survived from the total fresh cells counted. In these experiments the cell suspension volume was 2.5 ml.

Figure 1:
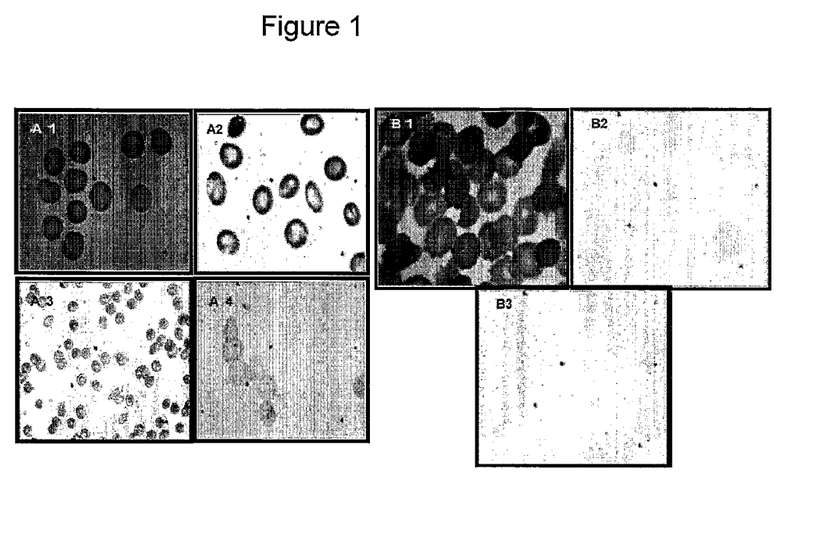
Figure 2:
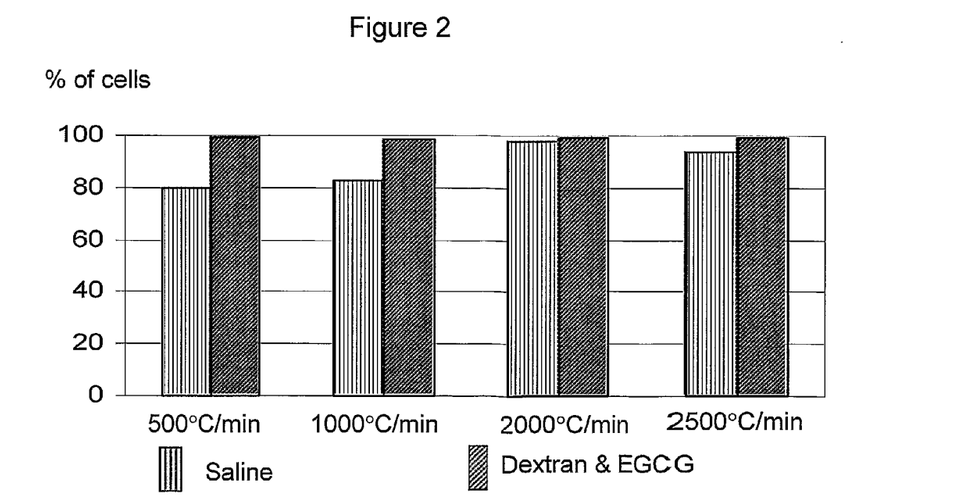
FIG. 2. this is FIG. 1. is a chart illustrating the survival of erythrocytes after freezing and thawing (freeze thawing) at different cooling rates with two different solutions at a volume of 9 ml.

FIG. 1 shows picture of samples that were frozen at 1,000° C./min and stained using May-Gruenwald Giemsa after thawing as described above.

TABLE II

| | RBC survival after Cryopreservation at 1,000° C./min | | | |
| --- | --- | --- | --- | --- |
| | 1,000° C./min | | 2,000° C./min | |
| Solution | 1A Thawed | 1B Rehydrated | 2A Thawed | 2B Rehydrated |
| PBS | 53.08 | 49.17 | 72.92 | 71.02 |
| Dextran | 98.7 | 69.95 | 98.28 | 71.92 |
| HSA + Trehalose | 97.7 | 55.20 | 99.26 | 70.79 |
| Trehalose | 89.04 | — | 93.24 | — |
| EGCG | 84.53 | 49.19 | 72.92 | — |
| EGCG + Dextran | 100 | 70.80 | 100.00 | 72.64 |
| EGCG + HSA + Trehalose | 98.6 | — | 96.20 | — |
| EGCG + Trehalose | — | 52.04 | 93.24 | 83.94 |

Under a light microscope or after May-Gruenwald Giemsa stains (FIG. 1), RBC that were frozen with EGCG and dextran appeared morphologically normal whereas in all other groups many irregular shaped cells were observed, as well as a lot of ghosts (i.e. cells whose membrane was damaged and the hemoglobin has leaked out but that did not undergo lysis). Apparently Pentra60 counts ghosts, therefore the additional morphological evaluations are important.

Example 2

Freezing RBC at a Volume of 9 ml

RBC were frozen at a volume of 9 ml using the MTG freezing apparatus at different cooling rates of 500, 1000, 2000 and 2500° C./min. Freezing solution was composed of 30% (w/v) dextran and 0.412 mM EGCG in PBS. Samples were thawed in a water bath at 37° C. After thawing, cells were counted using the is Pentra60 (ABX, France) and morphological observation was conducted using May-Gruenwald Giemsa stain and light microscopy.

Figure 3:
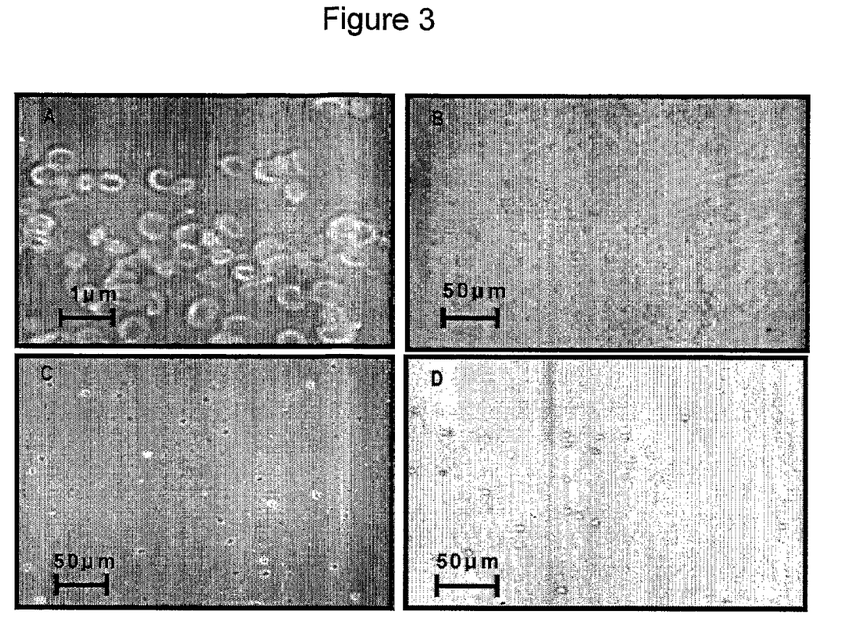
FIG. 3. shows light microscopy pictures taken after freeze thawing of 9 ml of erythrocytes at a cooling rate of 1000° C./min. A and B were frozen with a solution composed of Dextran and EGCG. C and D were frozen with saline.

Results are shown in FIGS. 1 and 3, wherein we can see that samples frozen with a solution composed of EGCG and dextran had higher viability rates as detected by the Pentra60 machine. In addition, morphological evaluations also showed that RBC frozen with EGCG and dextran had a substantially normal morphological appearance.

Example 3

Freezing RBC at a Volume of 50 ml

Figure 4:
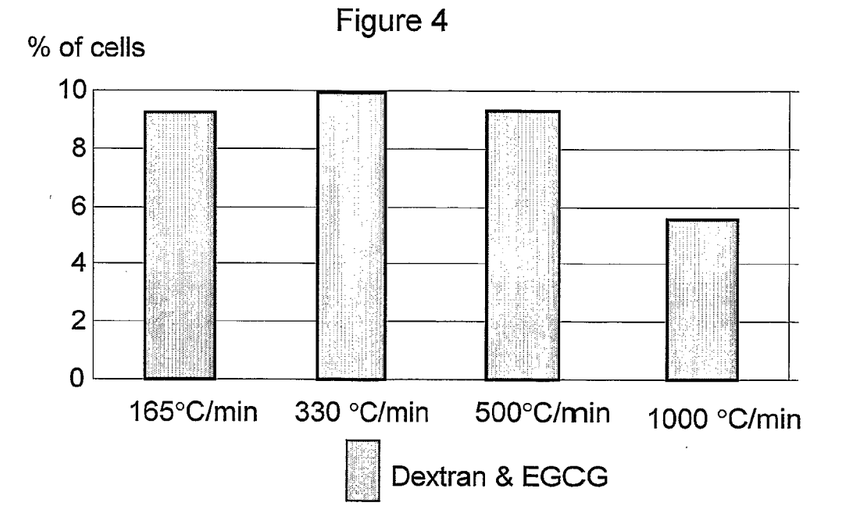
FIG. 4. is a chart illustrating the survival rate of erythrocytes after freeze thawing at a volume of 50 ml with a freezing solution containing Dextran and EGCG at different cooling rates.

RBC were frozen at a volume of 50 ml. Freezing using the MTG freezing apparatus at different cooling rate of: 165, 330, 500 and 1000° C./min. Freezing solution was composed of 30% (w/v) dextran and 0.412 mM EGCG in PBS. Thawing was done in a water bath at 37° C. Results are shown in FIG. 4.

The highest survival rate was achieved at a cooling rate of 330° C./min. This cooling rate is lower than that of the best cooling rate in previous experiments. This difference may be due to the significantly high volume of the sample. In large volume the heat transfer is slower; therefore at very high cooling rates a more significant thermal gradient develops across the sample. One method of avoiding these temperature differences and achieving better heat transfer along the sample is the use of lower cooling rates.

Example 4

Freezing RBC at a Volume of 200 ml

Figure 5:
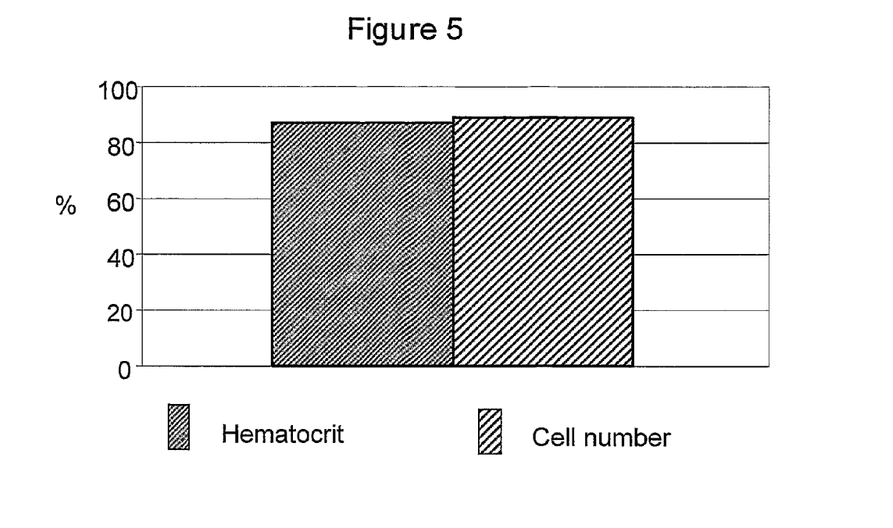
FIG. 5. is a chart illustrating the percentage of erythrocytes number and hematocrit after freezing 200 ml at a cooling rate of 315° C./min in a conventional freezing bag.

In this experiment we have frozen RBC in a cell suspension of 200 ml. Freezing solution was composed of 30% (w/v) dextran and 0.412 mM EGCG in PBS. The cell suspension was put in a 2000 ml volume freezing bag (Baxter-Fenwal, USA). The bag was placed in an MTG freezing apparatus. Freezing was done at a cooling rate of 330° C./min. Thawing was done as before in a water bath at 37° C. Cells were counted using the Pentra60 (ABX, France). Results are shown in FIG. 5 as a percentage of the fresh cell number and hematocrit. We can see that almost 80% of the cells survived when freezing 200 ml of RBC suspension. To the inventors best knowledge, such high viability rate in such large volume, when freezing a the cells without any intracellular cryoprotectants has been regarded as impossible, until now.

Example 5

RBC Hemolysis

In the following Examples, unless specifically said otherwise, free hemoglobin levels detection was done by using the cyanmethemoglubin assay using Drabkin's solution (Sigma, USA) and reading the absorbance at 540 nm using an ELISA reader (Bio Tek Instruments, USA). Hemoglobin (Hb) concentration was measured in the supernatant and in the pellet, and the hemolysis percentage was calculated using Formula I:

Calculation of hemolysis percentage   Formula I $$100 \times \frac{[(\text{supernatant } Hb)(\text{supernatant volume})]}{[(\text{total } HB)(\text{total volume})]}.$$

Example 5A

RBC Frozen in Different EGCG Concentrations

The freezing solution was composed of 20% (w/v) Dextran 40 (Amersham bioscience, USA) supplemented with 4.12 mM or 2.06 mM EGCG (>90% purity, Taiyo, China) in 0.8% NaCl (Sigma, USA) in double distilled water. Freezing solution was mixed in a 1:1 ration with packed red blood cells.

RBC were frozen at a volume of 2.5 ml in a 16 mm diameter test tube (Manara, Israel) using the MTG freezing device. The temperature gradient was 5° C. to −100° C., ice interface velocity was 3 mm/sec resulting in a calculated cooling rate of 1890° C./min. The test tubes were rotated during freezing at 60 rounds per minute. After freezing, samples were stored for 24 hours in a −80° C. freezer (Forma, USA). Thawing was performed by plunging the samples in a water bath at 37° C. for a period of time under a minute, when the samples visually appears to have been completely thawed.

Post thaw hemolysis levels were: 2.55% for RBC that was frozen in a solution having 2.06 mM EGCG and 3.5% for RBC that was frozen in a solution having 4.12 mM EGCG. When frozen in a solution of dextran in 0.8% NaCl only, post-thaw hemolysis exceeded 10%.

Example 5B

Post-Thaw Hemolysis Rate of RBC that were Frozen with Different Green Tea Extract (GTE) Concentrations GTE was purchased from Taiyo, China at a purity of ~80% catechins which contained the at least the following polyphenols: 48% EGCG, 10.8% epigallocatechin (EGC), 1.4% DL-Catechin (DL-C; (2S,3R)-2-(3,4-Dihydroxyphenol)-3,4-dihydro-1(2H)-benzopyran-3,5,7-triol), 5.6% epicatechin (EC). 2.6% gallocatechin gallate (GCG) and 14.5% epicatechin gallate (ECG). All other experimental conditions were as described in Example 5A.

The post-thaw hemolysis levels were calculated using Formula I to be 1.75, 1.5 and 2.56% for 0.47, 0.945 and 1.89 mg/ml GTE, respectively. These quantities of GTE are the equivalent of 1.03, 2.06 and 4.12 mM EGCG.

Example 5C

The Effect of the Thermal Gradient on Post Thaw Hemolysis Rates

The freezing solution was composed of 20% (w/v) dextran 40 (Amersham Bioscience, USA) supplemented with 2.06 mM EGCG (>90% purity from Taiyo, China) in 0.8% (w/v) NaCl (Sigma, USA) in double distilled water.

Ice interface velocity was 3 mm/sec and the following thermal gradients were evaluated: 5° C. to −100° C., 37° C. to −100° C. and 37° C. to −112° C., resulting in a calculated cooling rates of 1890, 2466 and 2680° C./min, respectively. Samples were rotated at 60 RPM. All other experimental conditions were exactly as described in Example 5A.

TABLE III

| | Post thaw hemolysis rates | | |
|---|---|---|---|
| Temperature gradient | 5° C. to −100° C. | 37° C. to −100° C. | Room temperature to −100° C. |
| % Hemolysis | 3.5 | 1.5 | 1.75 |

Example 5D

Post-Hydration Hemolysis Rate of RBC that were Freeze-Dried with Different EGCG Concentrations Packed RBC were mixed at a ration of 1:1 (v/v) with a freezing solution composed of 20% (w/v) Dextran 40 (Amersham bioscience, USA) supplemented with 1.03, 2.06 or 4.12 mM EGCG (>97% purity, Cayman, USA) in 0.8% (w/v) NaCl (Sigma, USA) in double distilled water.

Freezing was performed as described in Example 5A. After freezing, samples were transferred to a commercial lyophilizer (Labconco, USA). Samples were lyophilized for 72 hours, after which rehydration was performed by adding 2.4 ml double distilled water at 37° C. back to the samples. After rehydration samples were counted and mean cell volume (MCV) was measured using the Pentra 60 (ABX, France) automatic cell counter. Free hemoglobin levels were measured as described above and the hemolysis percentage was calculated using Formula I.

TABLE IV

| | Post thaw hemolysis rates | | | | | | |
|---|---|---|---|---|---|---|---|
| | number of Cells ($10^9$/ml) | | | MCV ($\mu m^3$) | | | % Hemolysis |
| EGCG | Fresh | Lyo* | %** | Fresh | Lyo | %** | in Lyo cells |
| 1.03 mM | 4.21 | 2.83 | 67.22 | 88 | 75 | 85.23 | 56.18 |
| 2.06 mM | 4.1 | 2.76 | 67.32 | 88 | 77 | 87.50 | 48.83 |
| 4.12 mM | 4.58 | 2.9 | 63.32 | 88 | 85 | 96.59 | 51.8 |

*The term "Lyo" denotes samples of cells that were lyophilized and rehydrated.
**These columns depict the percentage of lyo cells from the fresh cells of the same category As seen in Table IV, at a concentration of 2.06 mM in the freezing solution EGCG gave best results with only 48.8% hemolysis. In addition, cells number after rehydration in this concentration was 67% of the fresh control. It may be assumed that the counted cell number being larger than the calculated hemolysis rate may be due to the fact that the Pentra 60 counter counts also ghosts (i.e. RBC that are essentially depleted of hemoglobin). On the other hand, in terms of MCV best result was obtained using 4.12 mM EGCG.

Calculation of pellet hemolysis percentage  Formula II $$100 \times \frac{[(\text{supernatant } Hb)(\text{a-cellular volume of pellet})]}{[(\text{total } HB)(\text{a-cellular volume of pellet} + \text{cellular volume of pellet})]}$$

TABLE V

Separation & Hemolysis of thawed blood

| Dextran 20% EGCG 2 mM Centrifugation conditions | Donor 1 | | | Donor 2 | | |
|---|---|---|---|---|---|---|
| | Pellet HCT* | Sample's Hemolysis (%) | Pellet Hemolysis (%) | Pellet HCT* | Sample's Hemolysis (%) | Pellet Hemolysis (%) |
| 4° C. 1000 g 10 min | 55.1 | 20.55 | 11.18 | 41.6 | 12.13 | 9.72 |
| 4° C. 1500 g 10 min | 49.8 | 11.02 | 6.94 | 54.4 | 12.98 | 6.49 |
| 4° C. 2000 g 10 min | 56 | 14.22 | 7.22 | 52.4 | 12.01 | 6.44 |
| 4° C. 3000 g 10 min | 53.2 | 11.14 | 6.20 | 56.7 | 13.36 | 10.08 |
| 25° C. 1000 g 10 min | 55.6 | 11.87 | 6.04 | 57.7 | 13.36 | 6.04 |
| 25° C. 1500 g 10 min | 57.3 | 10.86 | 5.14 | 68.7 | 11.27 | 3.11 |
| 25° C. 2000 g 10 min | 63.3 | 11.05 | 4.13 | 74 | 9.9 | 2.10 |
| 25° C. 3000 g 10 min | 66.7 | 10.4 | 3.35 | 80.3 | 7.52 | 1.10 |
| 37° C. 1000 g 10 min | 62.7 | 11.73 | 4.51 | 63.3 | 10.37 | 3.68 |
| 37° C. 1500 g 10 min | 65.9 | 11.88 | 4.00 | 75.9 | 10.12 | 1.95 |
| 37° C. 2000 g 10 min | 70.5 | 11.65 | 3.19 | 74 | 9.23 | 1.94 |
| 37° C. 3000 g 10 min | 72.8 | 10.59 | 2.58 | 82.9 | 7.19 | 0.88 |

*hematocrit (HCT) - the percent of the sample that is composed of red blood cells

Example 5E

Separation of Free Hemoglobin from RBC

Two blood units, each from a different donor, were received from the Israeli blood bank. Each unit was centrifuged at 1500 rpm for 10 minutes. Plasma was discarded and PBS (Biological industries Beit Ha-Emek) was added. The suspension was centrifuged again (1500 rpm for 10 minutes) and the supernatant discarded. Freezing solution (20% (w/v) dextran 40 and 2 mM EGCG, dissolved in 0.8% NaCl DDW) was added to the pellet at a 1:1 ratio. 2.5 ml of the resulting samples were then frozen using the MTG-516 device. The thermal gradient was from room temperature to −100° C., ice interface velocity was 3 mm/sec, resulting at a calculated cooling rate of 2250° C./min. After freezing was completed samples were stored for 24 hours at −80° C. freezer (Forma, USA). Thawing was performed by plunging the test tubes into a water bath at 37° C. for no more than 1 minute until the sample appears visually to have been completely thawed. After thawing, 2 test tubes from each donor were combined for each of the centrifugation conditions, as depicted in Table V.

Hemolysis was calculated as follows: After centrifugation, a sample from each of the supernatant and pellet was taken and measured for hemoglobin, and the "Sample's Hemolysis" was calculated according to Formula I. In addition, the pellet was assayed for hematocrit (i.e. what part of the pellet volume is cellular). The hemoglobin (Hb) of the pellet comprises mainly hemoglobin within RBC and some that is free and is assumed to be of the same concentration as the supernatant. Thus the Pellet hemolysis was calculated according to the following Formula II.

Separation quality improved as a function of centrifugation temperature and relative centrifugal force (RCF). RCF of 3000 g at 37° C. has resulted with the best separation quality (cells number and HCT) and lowest hemolysis rates. Sample hemolysis values were also lower at the higher RCFs and the higher centrifugation temperatures.

Example 5F

Separation of Fresh Blood from Free Hemoglobin

Fresh blood, received from the Israeli blood services, was divided to 2 samples; one sample was left un-touched and the other was plunged into liquid nitrogen several times until full hemolysis was reached. Portions of the two samples were recombined in different proportions to achieve the following hemolysis rates: 5, 10 and 15%.

Combined samples were centrifuged at 3000 g for 10 minutes at 25° C. or is 37° C. As control fresh blood was centrifuged at the same conditions. Free hemoglobin levels were measured and calculated as described above in Example 5E.

TABLE VI

Separation & Hemolysis of Fresh blood

| | Sample's hemolysis | Pellet hemolysis |
|---|---|---|
| Fresh 25° C. | 0.25 | 0.02 |
| Fresh 25° C. + 5% hemolysis | 5.5 | 0.34 |
| Fresh 25° C. + 10% hemolysis | 12.3 | 1.19 |
| Fresh 25° C. + 15% hemolysis | 15.6 | 1.72 |
| Fresh 37° C. | 0 | 0 |
| Fresh 37° C. + 5% hemolysis | 8 | 0.65 |
| Fresh 37° C. + 10% hemolysis | 10.06 | 0.74 |
| Fresh 37° C. + 15% hemolysis | 19.06 | 2.94 |

From the sample's hemolysis results we can see that the measurements of free hemoglobin using Drabkin's solution were comparable to those expected. As can be seen, centrifugation of the samples allowed removal of the free hemoglobin. When the pre-centrifugation concentration of free hemoglobin was 8% or less (regardless of temperature) the post centrifugation concentration was 0.65% or less. Since the present invention provides thawed RBC samples that have less than 5% hemoglobin the post centrifugation packed RBC are expected to have even lower free hemoglobin (potentially less than 0.65% or even less than 0.35%).

In fact, at hemolysis rates of up to 8% (and even 10% in 37° C.) the separation resulting in less then 1% hemolysis (even less than 0.8%).

Example 6

Osmotic Fragility

Packed RBC were mixed in a ratio of 1:1 (v/v) with a freezing solution composed of 20% (w/v) dextran 40 kD supplemented with 0.9 mg/ml EGCG (>90% purity, Taiyo, China) and 0.8% (w/v) NaCl in DDW. The control group was whole blood. Portions of each of the EGCG supplemented and control were exposed to different sodium chloride concentrations of: 0.1, 0.2, 0.3, 0.4, 0.5, 0.6, 0.7, 0.8 and 0.9% (w/v).

Figure 8:
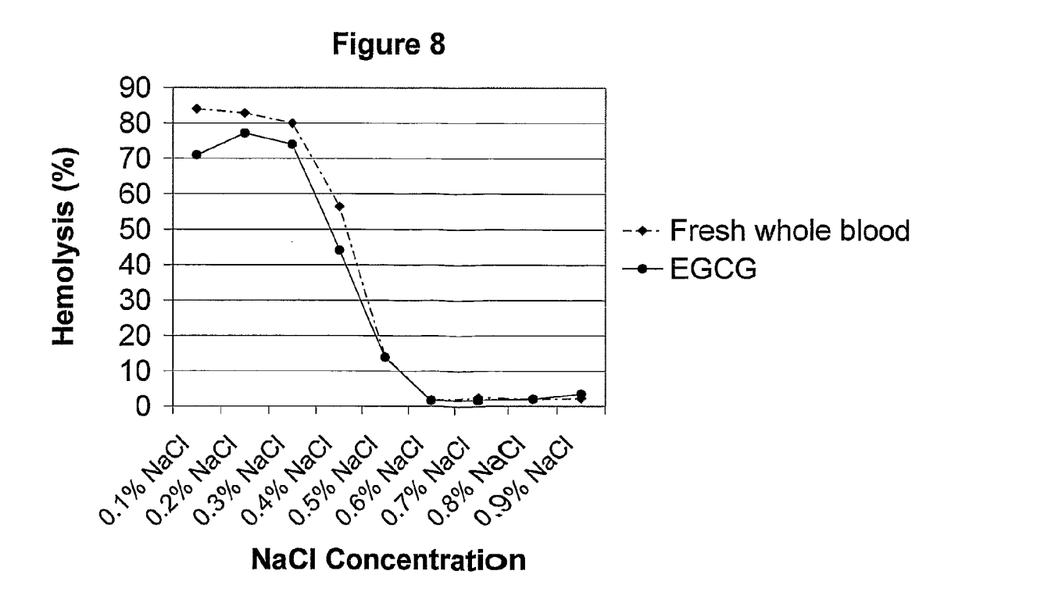
FIG. 8. is a chart showing the osmotic fragility assay results of fresh RBC and fresh RBC with EGCG at different NaCl concentrations and the effect of EGCG thereon.

Free hemoglobin was measured as described above and the hemolysis percentage was calculated using Formula I. The results of this experiment are shown in FIG. 8. We can see that for NaCl concentrations above 0.6% (w/v) no significant difference was detected between the control and EGCG. As the samples were exposed to increasing hypotonic environment (below 0.5% NaCl) the EGCG supplemented samples displayed lower hemolysis rates.

In conclusion, the addition of EGCG has changed the cells' durability at osmotic stress. This indicates that EGCG may have a stabilizing affect on the RBC membrane making it less susceptible to hypo-osmotic stress.

Example 7

Freezing RBC Without Thermal Gradients at Varying NaCl Concentrations

Packed RBC were mixed in a 1:1 ratio with freezing solutions composed of EGCG (2.06 mM), 20% (w/v) dextran 40 kD in different NaCl concentrations as detailed below. Samples volume was 1 ml. The Samples were maintained for at least 10 min at 5° C. and then transferred to a metal plate in a conventional freezing device (Forma, USA) at −80° C. for a period of 24 h. Samples were thawed by being placed in a 37° C. bath until they visually appeared to be thawed (less than 1 minute) and then counted and mean cell volume (MCV) was measured using the Pentra 60 (ABX, France) automatic cell counter. The results are summarized in Table VII. The percentage shown, is the thawed samples as compared with a fresh sample.

TABLE VII

Post thaw RBC cell number and MCV

| NaCl | MCV (µm³) | | | Cell Number (10⁹/ml) | | |
|---|---|---|---|---|---|---|
| Concentration | Fresh | Thawed | % | Fresh | Thawed | % |
| 0.6% | 89 | 107 | 120.22 | 4.12 | 4.12 | 100.00 |
| 0.7% | 90 | 112 | 124.44 | 4.27 | 4.27 | 100.00 |
| 0.8% | 90 | 107 | 118.89 | 4.71 | 4.71 | 100.00 |
| 0.9% (Saline) | 90 | 91 | 101.11 | 4.53 | 3.42 | 75.50 |

Example 8

Hypothermic Preservation of Red Blood Cells

Whole blood units, 2 days old, 500 ml each, were received from the Israeli blood services. 2 ml PBS were added to one bag and 2 ml PBS comprising 0.236 gram GTE (Taiyo, China) were added to the other. This GTE contains ~80% catechins which contained the at least the following polyphenols: 48% EGCG, 10.8% epigallocatechin (EGC), 1.4% DL-Catechin (DL-C; (2S,3R)-2-(3,4-Dihydroxyphenol)-3,4-dihydro-1(2H)-benzopyran-3,5,7-triol), 5.6% epicatechin (EC). 2.6% gallocatechin gallate (GCG) and 14.5% epicatechin gallate (ECG). The final concentration of GTE was 0.4725 mg/ml. During delivery and storage the blood was maintained in a refrigerator at 4° C. storage.

1 ml samples were taken from each bag at the following times: (a) when the units arrived, (b) 15 minutes after adding PBS of EGCG and (c) 1 week later. The samples were counted and the mean cell value was measured using the Pentra 60 (ABX, France). Cells counts and MCV were essentially the same in all samples.

ATP content of each sample was assayed using ATP Bioluminescence Kit CLS II (Roche, Switzerland) according to the manufacturer's manual. In this assay, light emission is in direct proportion to the amount of ATP in the sample. The intensity of the light was measured using a luminometer (Turner Biosystems, USA), and the results are summarized in Table VIII.

TABLE VIII

| ATP contents of stored RBC[M] | | | |
|---|---|---|---|
| Solution | Fresh | 15 min after add. | 1 week after add. |
| PBS | $2.2 \times 10^{-7}$ | $1.09 \times 10^{-7}$ | $0.52 \times 10^{-7}$ |
| PBS & EGCG | $2.0 \times 10^{-7}$ | $1.07 \times 10^{-7}$ | $1.64 \times 10^{-7}$ |

Example 9

Prolonged Storage of Frozen RBC

In this set of experiments packed RBC were mixed in a 1:1 ratio with freezing solutions composed of 20% (w/v) dextran 40 kD in 0.8% NaCl with 2.06 mM or 4.12 mM EGCG (Cayman, USA). Packed RBC that were only mixed with a solution composed of 20% (w/v) dextran 40 kD in 0.8% NaCl and 0.8% NaCl were used as control. Sample volume was 1 ml.

Freezing was done directionally using the MTG apparatus at a calculated cooling rate of 1890° C./min. Storage was done in a −80° C. freezer (Forma, USA). Samples were taken out after different storage periods of: 24 hours, 1 week or 8 weeks. After thawing in a water bath at 37° C. until the samples visually appeared to be thawed, samples were counted and MCV was evaluated using Pentra 60 (ABX, France). ATP was evaluated as described above and free hemoglobin evaluations were performed as described in Example 5.

The results are presented in Table IX (cell numbers) Table X (MCV) and Table XI (hematocrit). Results are presented as the percentage of cells number and MCV as compared to fresh levels.

TABLE IX

Cell Numbers of Cells preserved for different periods

| Cells number (%) | Thawed after 24 hrs. | Thawed after 1 week | Thawed after 8 weeks |
|---|---|---|---|
| 20% Dextran | 99.25 | 99.00 | 100.00 |
| 20% Dextran & x5 EGCG | 99.76 | 98.80 | 99.52 |
| 20% Dextran & x10 EGCG | 99.35 | 100.00 | 98.92 |
| Saline | 56.17 | 74.02 | 65.35 |

TABLE X

MCV of Cells preserved for different periods

| MCV (%) | Thawed after 24 hrs. | Thawed after 1 week | Thawed after 8 weeks |
|---|---|---|---|
| Dextran | 117.98 | 121.35 | 111.24 |
| 20% Dextran & x5 EGCG | 101.12 | 101.12 | 104.49 |
| 20% Dextran & x10 EGCG | 101.12 | 100.00 | 100.00 |
| Saline | 94.32 | 100.00 | 96.59 |

TABLE XI

Hematocrit of Cells preserved for different periods

| % Free Hb | Fresh | Thawed after 24 hrs. | Thawed after 1 week | Thawed after 8 weeks |
|---|---|---|---|---|
| Dextran | 0 | 35.73 | 37.22 | 22.08 |
| 20% Dextran & x5 EGCG | 2.84 | 8.93 | 5.21 | 12.41 |
| 20% Dextran & x10 EGCG | 1.42 | 11.41 | 7.94 | 13.24 |
| Saline | 0.71 | 66.50 | 55.20 | 48.33 |

2. Mononuclear Cells

Example 10

Mononuclear Cells (MNC) Derived from Umbilical Cord Blood (UCB)

Blood was separated on ficoll-paque gradient for 30 minutes at 1000 g. Afterwards the mononuclear layer was drawn out and washed twice in PBS for 10 minutes at 200 g. To each pellet one of the following freezing solutions was added:
1) 0.1M Trehalose, 12.5% (w/v) HSA in PBS.
2) 0.1M Trehalose, 12.5% (w/v) HSA and 0.412 mM EGCG in PBS.
3) 12.5% (w/v) HSA and 0.412 mM EGCG in PBS.
4) 51.5 μM EGCG with 0.1M trehalose PBS.
5) 30% (w/v) Dextran with 0.412 mM EGCG in PBS.

Freeze Thawing and Freeze Drying 2.5 ml of cell suspension were put in a 16 mm diameter glass test tube (Manara, Israel) and frozen using the MTG freezing apparatus (IMT, Israel). The temperature gradients were 1.5° C./mm and 0.428° C./mm, velocity was 0.2 mm/sec resulting in a cooling rate of 18° C./min and 5.1° C./min respectively. The first cooling rate was applied until the seeding temperature was reached. The samples were rotated at 56 rounds per minute (RPM).

After freezing samples were plunged into liquid nitrogen (LN), and then samples were either thawed at 37° C. in a water bath or put in a commercial lyophilizer (Labconco, USA) with a condenser temperature of −80° C. After drying the cells were rehydrated with DDW at 37° C. Cells that were frozen and did not undergo lyophilization were thawed in a water bath at 37° C.

Assessment of Cell Survival

Cells were counted using the PENTRA 60 cell counter, as described above. viability assessments were performed by evaluating the cells' membrane integrity using SYBR14 plus Propidium Iodide (PI) (Molecular Probes, USA) live/dead fluorescent staining. These stains are nucleic acid stains, SYBR14 is a membrane permeable molecule and PI can enter the cell only if the membrane is damaged.

Results

Figure 6:
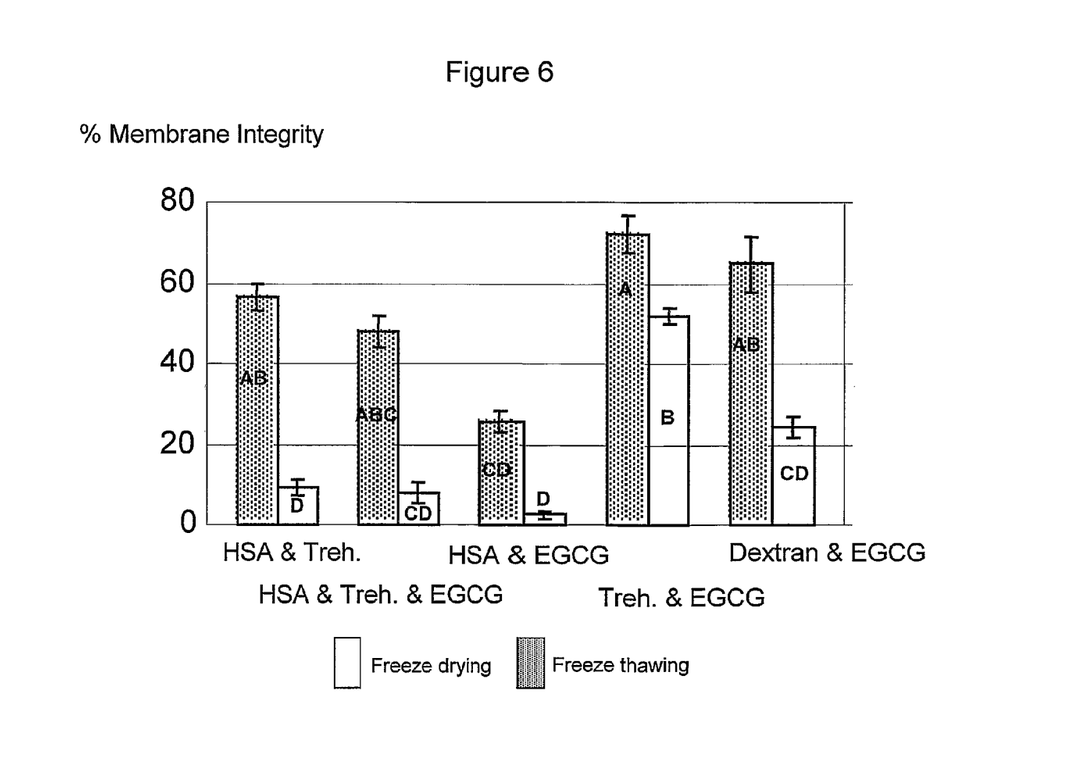
FIG. 6. is a chart illustrating the mononuclear cells (MNC) derived from umbilical cord blood (UCB) frozen with different solutions and then thawed or dried.

A. The viability of the cells after freezing and freeze drying with different freezing solutions (as described above) was assayed. FIG. 6 shows the viability rates as demonstrated by membrane integrity of the cells. FIG. 6 shows that the solution composed of EGCG and trehalose gave best results after freeze thawing and freeze drying.

Figure 7:
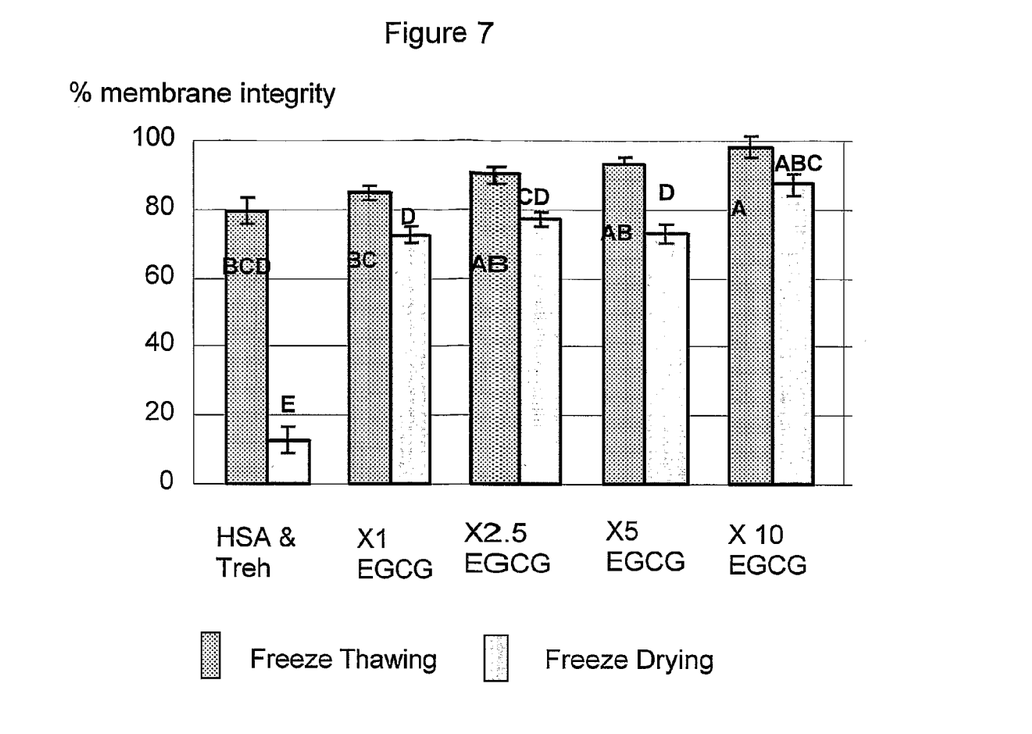
FIG. 7. is a chart illustrating MNC derived from UCB after freeze thawing and freeze drying with different concentrations of EGCG. X1 EGCG=0.412 mM EGCG; HSA & Trehalose were in a concentration of 0.1M Trehalose and 12.5% (w/v) HSA in PBS ($Ca^{+2}$ & $Mg^{+2}$ free).

B. The effect of different EGCG concentrations in a solution comprising EGCG and trehalose was evaluated. The EGCG concentrations were: 0.412 (×1 EGCG), 1.03 (×2.5 EGCG), 2.06 (×5 EGCG) and 4.12 mM EGCG (×10 EGCG), each with 0.1M trehalose in PBS. As a control we used a solution composed of 0.1M trehalose and 12.5 (w/v) Human serum albumin (HSA). FIG. 7 indicates that viability increased with EGCG concentration after freeze thawing and after freeze drying.

C. In this example a freezing solution composed of 0.1M Trehalose and either 0.47 mg/ml EGCG (×2.5) or 1.89 mg/ml EGCG (×10) in PBS was used. Samples volume was 2.5 ml and samples were frozen as described above and then lyophilized. After being in the lyophilizer for 72 h, the samples were taken out and rehydrated with 2.4 ml of DDW at 37° C. After rehydration samples were assayed for CD3 using FACS (fluorescent-activated cell sorter) in accordance with the method described in Huiling et al. The Journal of Immunology 2003, 171: 4824-4829, with minor modifications.

CD3 is a known cellular marker that is present in mature lymphocytes but not in other mononuclear cells, thus its presents indicates that mature lymphocytes are present in the sample.

Membrane integrity of the samples was evaluated before and after rehydration using SYBR 14 and PI (Molecular Probes, USA). The membrane integrity and CD3 expression results are summarized in Table XII.

TABLE XII

Membrane Integrity and CD3 expression of UCB derived MNC

| Solution | Sample No. | Mambrane integrity (%)* | CD3 (%) |
|---|---|---|---|
| Fresh with 0.47 mg/ml EGCG | 1 | 97.36 ± 2.2 | — |
| Lyophilized with 0.47 mg/ml EGCG | 1 | 55.1 ± 8.5 | 80 |
|  | 2 | 59.8 ± 1.4 | 80 |
| Fresh with 1.89 mg/ml EGCG | 1 | 90.01 ± 4.3 | — |
| Lyophilized with 1.89 mg/ml EGCG | 1 | 79.31 ± 8.8 | 81 |
|  | 2 | 83.62 ± 5.7 | 83 |
|  | 3 | 88.4 ± 3.2 | 82 |
|  | 4 | 88.03 ± 5.6 | 78 |

*The membrane integrity results in each row each represent the results from at least 300 cells in 3 different places in the slide.

Figure 9:
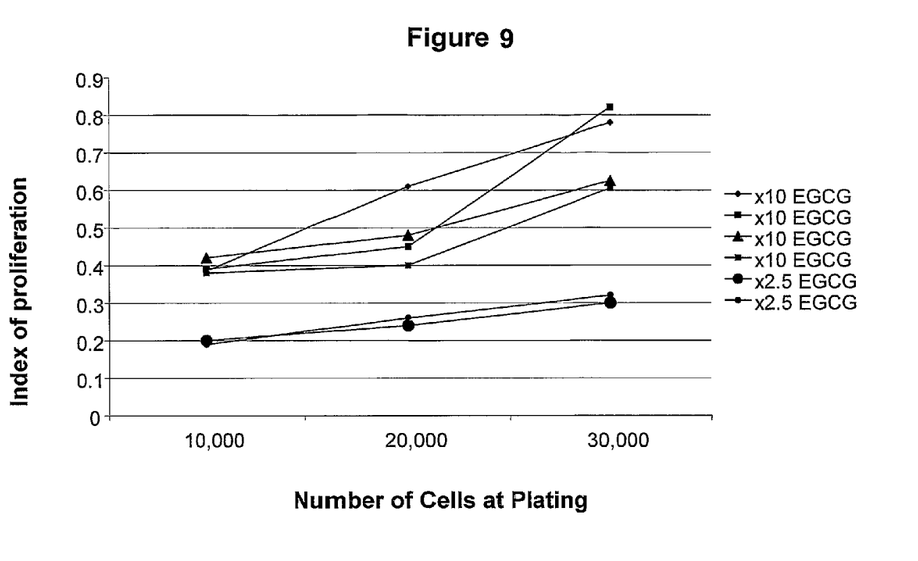
FIG. 9. is a graph showing the proliferation of mononuclear cells (MNC) after freezing and thawing and after lyophilization and re-hydration, according to some embodiments of the invention. (×2.5 EGCG=1.03 mM; ×10 EGCG=4.12 mM)

In addition, a cell proliferation assay was performed. In brief, the hydrated cells were incubated for 48 hour after which a proliferation assay based on thymidine incorporation was carried out (Promega, USA). The results of the proliferation assay are depicted in FIG. 9, wherein the proliferation index of the cells is depicted as a function of their number at initial plating. As can be seen all cells lyophilized at a concentration of ×10 EGCG depicted a higher proliferation index than those lyophilized in ×2.5 EGCG. In addition, as the cells' initial plating number increases so does the proliferation index. The almost linear proportion shown for one of the ×10 EGCG samples is similar to that observed with fresh cells 3. Bacteria Example 11

Freeze Drying of E-coli

E. coli were placed in LB medium: 10 gr Bacto-tryptone (Difco, USA), 5 gr yeast extract (Difco, USA), 10 gr NaCl, in 1 liter distilled water. The total volume of 10 ml was divided to two batches of 5 ml each. To the first batch of E. coli in LB medium we added 5 ml of freezing solution composed of 30% (w/v) dextran and 1.03 mM EGCG (Cayman Chemical, USA) in PBS. The other batch was left un-touched. Cell-suspension samples of 2.5 ml each (two from each batch) were put in 16 mm diameter glass test tubes (Manara, Israel), such that a total of 4 test tubes were prepared. The test tubes were frozen at 1000° C./min (from 5 to −50° C. at a velocity of 3 mm/sec and with 56 RPM. After freezing was completed the test tubes were placed in liquid nitrogen. Afterwards, the 4 test tubes were placed in a lyophilizer (Labcono, USA) for 72 hours. After lyophilization was completed the "powdered" cells from each test tube were scraped into a petri dish. An hour later 2 ml of DDW at 37° C. were added to each dish. From each dish 3 petri dishes with agar were plated. The following Agar plates protocol was used: 10 gr Bacto-tryptone, 5 gr yeast extract, 10 gr Na $^+$Cl$^-$, 10 gr agar (BD, USA). Water was added to a volume of 1 liter, autoclaved, cooled to 65° C. and poured into petri dishes. A total of 12 petri dishes were incubated at 37° C. for 24 hours. The next day colonies were counted. Table XIII depicts the number of colonies grown on the agar petri dishes. As seen in Table XIII, E. coli colonies were observed in all plates, and the addition of Dextran and EGCG improved the bacteria's survival of lyophilization.

TABLE XIII

Number of E. coli colonies after being frozen with different freezing solutions and lyophilized

| E. coli frozen in LB | E. coli frozen with dextran and EGCG |
|---|---|
| 36 | 152 |
| 24 | 220 |
| 16 | >200 |

The invention claimed is:

1. A method for preserving red blood cells (RBC), comprising:
adding a preservation solution to the RBC, the preservation solution comprising one or more polyphenols;
freeze drying the RBC to produce frozen RBC; and
storing the frozen RBC under appropriate storing conditions,
wherein, post preservation, the RBC comprise free hemoglobin levels below 10 percent.

2. The method of claim 1, wherein the polyphenols comprise one or more catechins.

3. The method of claim 2, wherein at least one of the one or more catechins is epigallocatechin gallate (EGCG).

4. The method of claim 1, wherein the polyphenols are derived from green tea extract (GTE).

5. The method of claim 1, wherein the preservation solution does not comprise a significant amount of glycerol.

6. The method of claim 1, wherein the preservation solution does not comprise a significant amount of DMSO.

7. The method of claim 1, wherein the preservation solution comprises a macromolecule.

8. The method of claim 1, wherein the preservation is cryopreservation, the preservation solution is a cryopreservation solution and the freeze drying is to a temperature below 0° C.

9. The method of claim 1, wherein the one or more polyphenols are present in the preservation solution at a concentration of from about 50 µM to about 4 mM.

* * * * *